United States Patent
Swanson et al.

[19]

[11] Patent Number: 6,112,183
[45] Date of Patent: Aug. 29, 2000

[54] METHOD AND APPARATUS FOR PROCESSING HEALTH CARE TRANSACTIONS THROUGH A COMMON INTERFACE IN A DISTRIBUTED COMPUTING ENVIRONMENT

[75] Inventors: Michael L. Swanson, Scandia; Denise Probst, Arden Hills; Paul M. Roberts, St. Louis Park; Lori A. Katainen, Eden Prairie; Roberta J. Pett, Lino Lakes; Mark W. Gladding, Elk River, all of Minn.

[73] Assignee: United Healthcare Corporation, Minneapolis, Minn.

[21] Appl. No.: 08/797,213

[22] Filed: Feb. 11, 1997

[51] Int. Cl.$^7$ .................................................. G06F 13/38
[52] U.S. Cl. ...................... 705/2; 705/3; 395/200.31; 395/200.33; 395/683; 395/684; 707/3
[58] Field of Search .................... 395/200.31, 200.33, 395/200.57, 683, 684; 707/3, 10, 104

[56] References Cited

U.S. PATENT DOCUMENTS

| | | |
|---|---|---|
| 5,524,253 | 6/1996 | Pham et al. . |
| 5,560,005 | 9/1996 | Hoover et al. . |
| 5,566,302 | 10/1996 | Khalidi et al. . |
| 5,675,805 | 10/1997 | Boldo et al. . |
| 5,691,601 | 11/1997 | White ........................................ 395/671 |
| 5,724,575 | 3/1998 | Hoover et al. ........................... 395/610 |
| 5,737,607 | 4/1998 | Hamilton et al. . |
| 5,740,427 | 4/1998 | Stoller ...................................... 395/615 |
| 5,754,772 | 5/1998 | Leaf ..................................... 395/200.33 |
| 5,781,743 | 7/1998 | Matsuno et al. ..................... 395/200.58 |

*Primary Examiner*—Allen R. MacDonald
*Assistant Examiner*—Jagdish Patel
*Attorney, Agent, or Firm*—Merchant, Gould, Smith, Edell, Welter & Schmidt, P. A.

[57] ABSTRACT

An apparatus and method for processing health care transactions through a common interface in a distributed computing environment using specialized remote procedure calls. The distributed computing environment includes a user interface tier for collecting user inputs and presenting transaction outputs, a data access tier for data storage and retrieval of health care transaction information, a transaction logic tier for applying a predetermined set of transaction procedures to user inputs and health care transaction information resulting in transaction output, an electronic network connecting the user interface tier, data access tier and transaction logic tier to each other and a communication interface for exchanging health care transaction information among the tiers. The communication interface includes an interface definition language generating transaction-specific communication codes whereby data is exchanged through a common interface structure regardless of the origin of the data.

11 Claims, 10 Drawing Sheets

METHOD AND APPARATUS FOR PROCESSING HEALTH CARE TRANSACTIONS THROUGH A COMMON INTERFACE IN A DISTRIBUTED COMPUTING ENVIRONMENT

FIELD OF THE INVENTION

The present invention relates generally to the field of computer-implemented data processing systems. More specifically, the present invention is directed to an apparatus and method for processing health care transactions through a common interface in a distributed computing environment.

BACKGROUND OF THE INVENTION

The use of computer systems to process health care transactions is widespread. This is the problem. Each generator of health care transactions stores information particular to its needs in a database format optimized for its processes in a computer environment developed from its technical skill level, growth and history.

For example, hospitals store a wealth of information on each patient, health care provider and medical intervention occurring within its walls. Hospitals store information such as, for example, in-patient and out-patient records (including patient charts), doctor privileges, nurse care schedules, operating room schedules and equipment inventories. Traditionally, hospitals transmit only as much of this information to health care insurers as needed to be reimbursed for health care costs.

In another example, physician offices also keep electronic records on each patient. Such information may include patient's personal data, patient immunization records, patient health history records and details about each patient visit. Again, health care providers typically transmit only as much of this information to health care insurers as needed to be reimbursed for health care costs.

In another example, dental offices also keep electronic records on each patient. Such information may include patient's personal data, patient dental cleaning history, records of upcoming appointments, patient health history records and details about each patient visit. Again, dental care providers typically transmit only as much of this information to health care insurers as needed to be reimbursed for dental care costs.

In yet another example, pharmacies keep electronic records concerning patient prescriptions, patient allergies and patient personal data. Again, pharmacies typically transmit only as much of this information to health care insurers as needed to be reimbursed for pharmacy costs.

The information requesting reimbursement for health care provided to a patient typically is transferred to the health care insurer in the form of a claim. The exact format of a claim takes many different electronic forms depending on the entity that generates the claim. A health care provider entity may be, for example, a hospital, physician office, dentist office or pharmacy. In addition, some claims pass through third party claims clearinghouses before being accepted by the health care insurer which may further change their electronic format. Payment obligations may pass to claims clearinghouses, other insurers, or a financial institution.

The data transfer itself may occur through very different transfer protocols and data error detection processes resulting in transforming data into even different formats.

The difficulty of communicating among different types of information stored in different electronic structures in different electronic environments is compounded when that information may be encrypted and/or compressed as well using different encryption and compression schemes.

In addition, the information itself may be stored in different human languages. Claims generating from a hospital in France are written in French in addition to the French data being encoded in a different database format in a different computer environment. For example, the common format for recording a date in the United States is month/day/year but in Europe, the common format is day•month•year. Though a perhaps minor difference, the erroneous transposition of the month and day in a data format would seriously undermine the integrity of all the records of an entire file.

There is a continued need for a system capable of communicating between a multiplicity of different computer environments.

SUMMARY OF THE INVENTION

The present invention is an apparatus and method for processing health care transactions through a common interface in a distributed computing environment. In particular, the present invention provides seamless communication between different computer systems and the data stored within each system through the use of specialized remote procedure calls.

It is a primary objective of the present invention to provide a common interface structure for processing health care transactions, regardless of the data's native format, compression, encryption, native language, country of origin, or operating environment of origin.

It is another objective of this invention to minimize computing time and resources in processing health care transactions.

It is a further objective of this invention to provide flexible system architecture for processing health care transactions in a constantly changing world.

DETAILED DESCRIPTION OF THE INVENTION

Figure 1A:
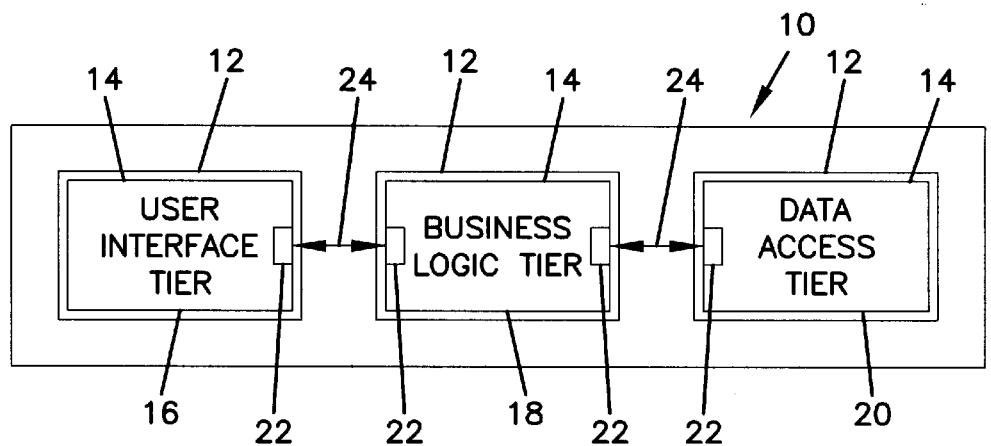
FIG. 1A is a block diagram showing the computer processing system of the preferred embodiment of the present invention.

The present invention provides a system for processing health care transactions in response to a user's request in a heterogeneous computing network. This is accomplished with an international managed care administrative system architecture.

The preferred embodiment of the present invention is implemented in a heterogeneous computer network environment that divides applications into parts or tiers that can be run independently on multiple systems that are connected via a network. More specifically, referring now to the drawings, wherein like reference numerals denote like elements throughout the several views, FIGS. 1A and 1B show block diagrams of a computer network 10 including several networked systems 12.

The applications 14 operating within systems 12 are developed using a three-tiered architecture. Each network system 12 implements applications 14 including a user interface tier 16, business logic tier 18, data access tier 20 and communication interface 22. The systems 12 are connected through a network connection 24.

Figure 1B:
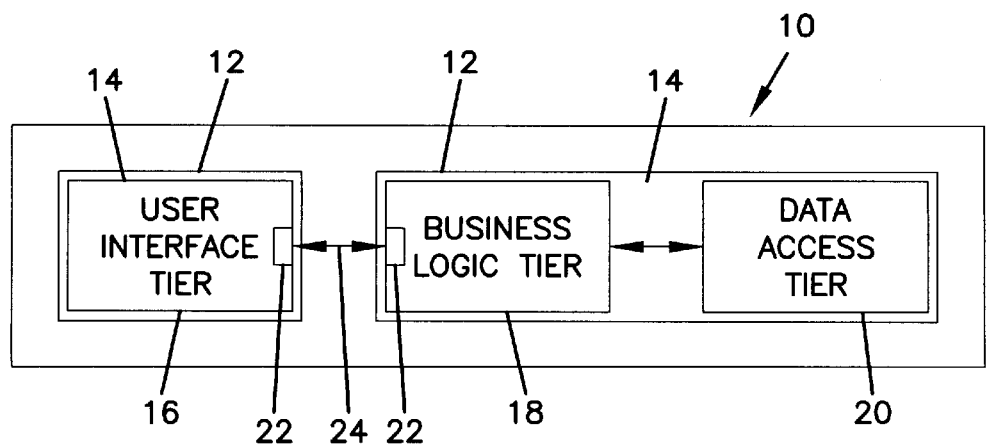
FIG. 1B is a block diagram showing the computer processing system of an alternate embodiment of the present invention.

Each application tier 16, 18, 20 may be implemented on a separate computer system 24 within the network system 12 such as shown in FIG. 1A. The computer system 12 running one application tier may be completely different from the computer system on which another tier is running. In the preferred embodiment, referring to FIG. 1A, each application tier 16, 18, 20 is implemented on an independent computer system 12 networked in a client/server environment. In an alternated embodiment, one or more of the application tiers 16, 18, 20 may be running in the same computer system 12 as shown in FIG. 1B.

In the context of this disclosure, the systems 12 to which the terms client and server are attached include programs that are running on some machine connected to a network. More specifically, a "server" is a program that advertises services it is capable of providing and a "client" is any program that requests services from one or more servers. In many cases a server is also a client of other servers in the network 10.

In the preferred embodiment, user interface tier 16 is implemented on a personal computer providing a graphical user interface (GUI). More specifically, in the preferred embodiment, the personal computer functions under an operating system consistent with Microsoft Windows operating system standards and is configured, at a minimum, with an Intel '386 processor chip or its equivalent and 8 MB RAM.

Business logic tier 18 is implemented on a server system in the preferred embodiment. It is understood that the server system may be a computer system 12 of any size from personal computer to mainframe to supercomputer depending on the computer resources required. In the preferred embodiment, the business logic server system is implemented on Unix computer systems, such as, IBM RS/6000 running AIX 3.2.5 and programmed in ANSI C and SQL (Structured Query Language).

Data access tier 20 is implemented in a database system. It is understood that the database system can be maintained in a computer system 12 of any size from personal computer to supercomputer, depending on the nature and volume of the data stored. In the preferred embodiment, the database system is a relational database server utilizing SQL for database access, such as the one vended by Sybase Corporation, in a UNIX operating environment.

The use of the three-tiered architecture accommodates the scalability of applications. Desired functionality extends to operate on a number of computer systems 12 throughout the network. Portability of applications from one system 12 to another is enhanced within the three-tiered architecture of the distributed computer network environment because of the modular structure of the applications. The modular design encapsulates each application 14 and its operation such that much of the application's operation and implementation information is hidden from a user. Each application 14 uses an interface to present its abstractions cleanly with no extraneous implementation information. Thus, applications are scalable to the environment in which they reside as long as a clean interface is maintained.

Communication interface 22 provides the standard mechanism for inter-tier communication. Rigorous definition of the communication interface 22 allows one tier of an application to be replaced without effecting other tiers. The replaced portion of the application is kept current with the latest technologies without requiring rewriting of an entire application each time one part is upgraded. For example, the user interface tier 16 can be independently replaced with a different technology or system 12 without affecting the business logic 18 or data access 20 tiers.

In the preferred embodiment, communication interface 22 is implemented via remote procedure calls (RPCs). The RPCs are implemented through the use of Open Environment Corporation's (OEC) Entera product consistent with Open Software Foundation's Distributed Computing Environment (DCE). DCE defines a vendor-independent definition of RPC communication in a heterogeneous, distributed network. Use of DCE provides a robust, open systems definition for client/server communications. In the preferred embodiment, the communication interface 22 transfers data among the tiers 16, 18, 20 over standard TCP/IP (Transmission Control Protocol/Internet Protocol) connections. Tiers 16, 18, 20 provide processing for health care transactions.

Figure 2:
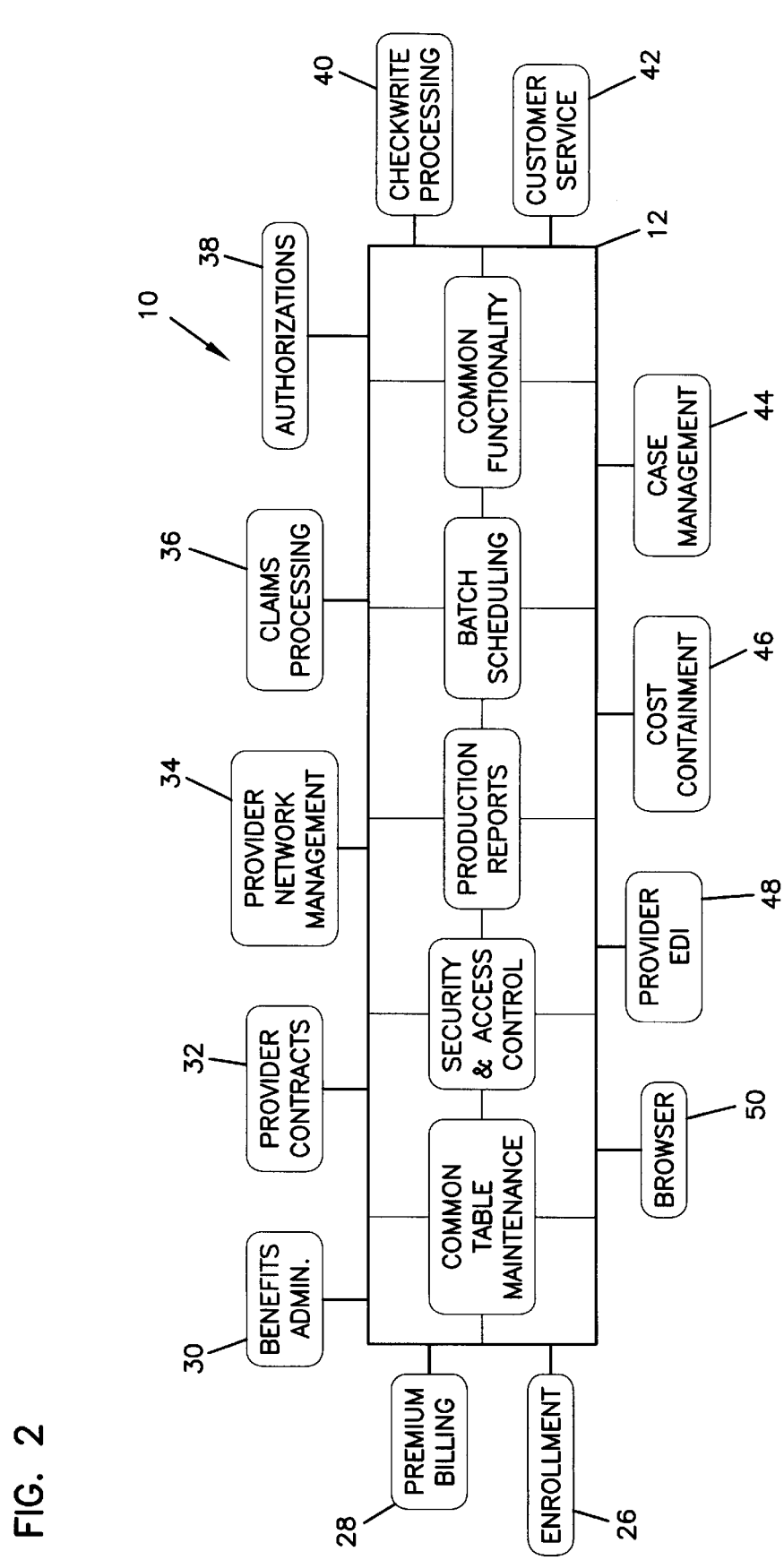
FIG. 2 is a block diagram showing different subsystems operating with the computer processing architecture depicted in FIG. 1.

Referring to FIG. 2, health care transactions can originate from many different sources or clients, such as, for example, enrollment subsystems 26, billing subsystems 28, benefits subsystems 30, provider contracting subsystems 32, provider network management 34, claims processing subsystems 36, security and authorization subsystems 38, check processing subsystems 40, customer service subsystems 42, case management subsystems 44, cost containment subsystems 46, provider electronic data interchange (EDI) subsystems 48 and/or browser subsystems 50. It is understood that each subsystem 26–50 may be maintained on completely different computer hardware systems from the other subsystems. Each hardware configuration operates with its own operating system environment storing information in potentially widely varying data formats.

Depending on the health care transaction processed, the client request for the transaction service is sent to an appropriate server for the requested information. Servers include, for example, the business logic tier 18 and data access tier 20 of the enrollment subsystems 26, billing subsystems 28, benefits subsystems 30, provider contracting subsystems 32, provider network management 34, claims processing subsystems 36, security and authorization subsystems 38, check processing subsystems 40, customer service subsystems 42, and case management subsystems 44.

The requests for transaction service are generally implemented as remote procedure calls (RPCs). Remote procedure calls are ideally suited to handling multiplicity of health care transactions. Once modified to handle health care transactions, RPCs provide a method for communication among systems with very different types of data maintained in very different formats and computing environments while maintaining the integrity and character of that data. Though the client request is generated in one computer system 12 or subsystem 26–50 and the requested information lies within another computer system 12 or subsystem 26–50, the communication interface 22 provides a common interface for completing the transaction service requested by the RPC.

Figure 3:
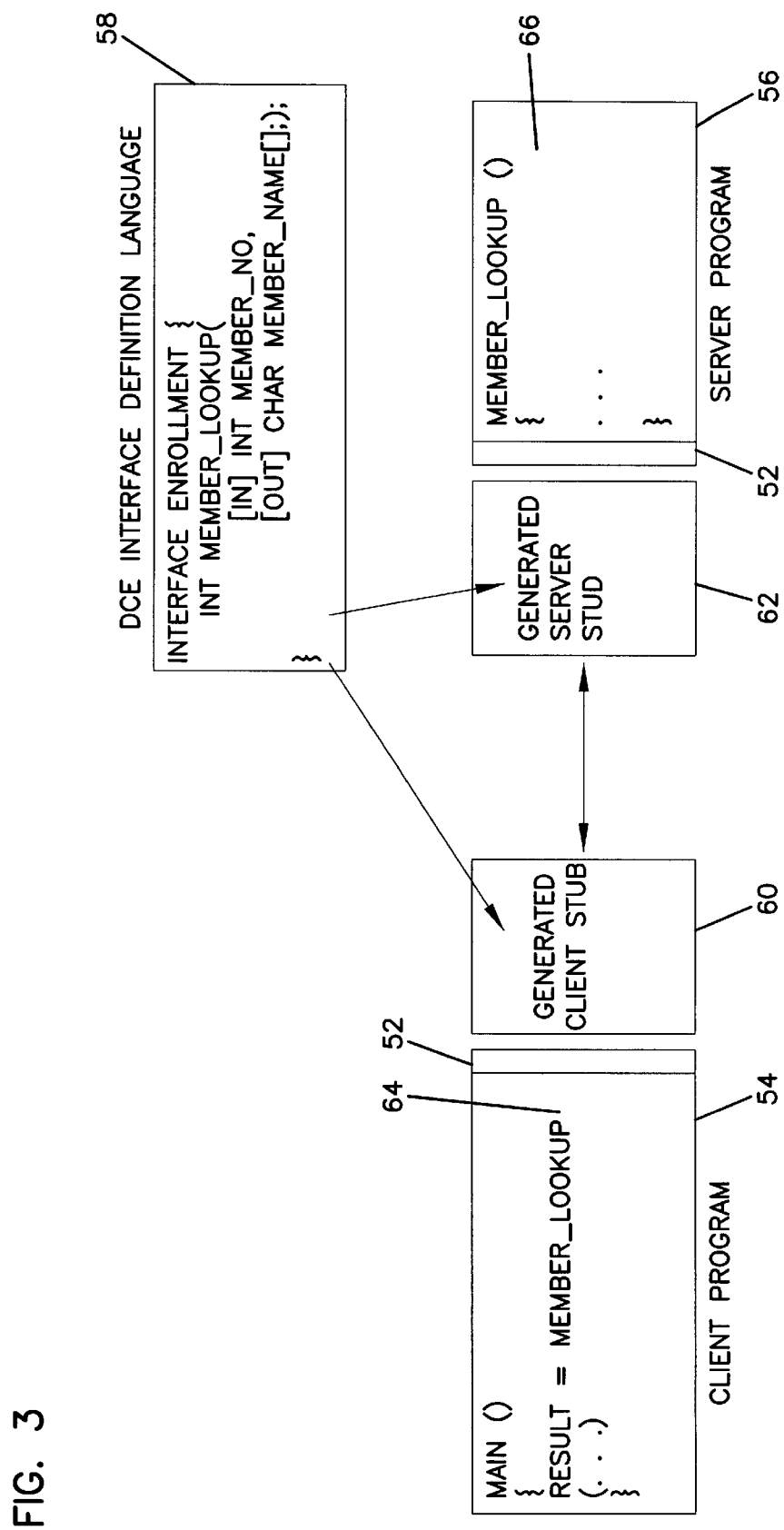
FIG. 3 is an illustration of example service requests generated in accordance with the present invention.

More specifically, referring to FIG. 3, as each application within tier 16, 18, 20 is added to network 10, an interface communication file 52 is created for each client program 54 and each remote server procedure 56. The interface communication file 52 generates communications code 58. The generated communications code 58 is referred to as client stubs 60 and server stubs 62. In the preferred embodiment, client stub 60 and server stub 62 are incorporated into applications 54, 56. With OEC Entera product, client stubs 60 are generated in PowerBuilder™, C, or perl, depending on the need. Server stubs 62 are generated in C and perl.

Use of a common communication interface 22 in the system architecture of the present invention enables the use of open systems technologies, adherence to international data processing standards and internationalization standards while utilizing an architecture that promotes vendor independence. This distributed computing model can operate in both a local area network as well as over a wide-area network or over the Internet.

In the preferred embodiment, the RPCs have been modified to generate health care transaction-specific client stubs 60 and server stubs 62. The client and server stubs generators 52 are incorporated into applications during the compilation process. More specifically, the incorporation process occurs automatically through the use of specialized compilation tools.

In particular, the specialized compilation tools have been implemented as a set of makefile templates for use in building servers. The makefile templates primarily contain macro definitions for the UNIX MAKE facility. These definitions provide information required by MAKE to compile and package a server. Sample makefile templates with common rules to build servers and clients are included in Appendix A.

It is understood that the contents of any macro will change depending on the application developed. For example, typical macros in the makefile templates include macros named SERVER, DB_NAME, APPL_NAME. The SERVER macro defines the name of the server. The DB_NAME macro defines the name of the database to be accessed by an SQL server. The APPL_NAME macro defines the name of the application. The particular macros used and the values assigned to them vary according to the type of server. For example, a server build in an SQL environment with C code uses one makefile template while a server built with embedded SQL requires a different template and a server built using C code uses a different template.

Once a server is built and logged on to the network 10, the server is ready to process requests from a client. The type of requests that the server will process depends on whether the server supports applications 14 for the user interface tier 16, business logic tier 18 or data access tier 20.

In operation, when a client makes a request for a service from a server, communication interface 22 provides the information to the server in the format that it requires to perform the service requested. More specifically, the communication interface 22 connects the client with the appropriate server and passes information between the server and client through client/server stubs 60, 62 generated during the request process. The client/server stubs 60, 62 are generated from interface specifications 52 coded during the compilation process according to the makefile templates. This generated stub code insulates the application developer from the underlying complexities of network programming.

Figure 4:
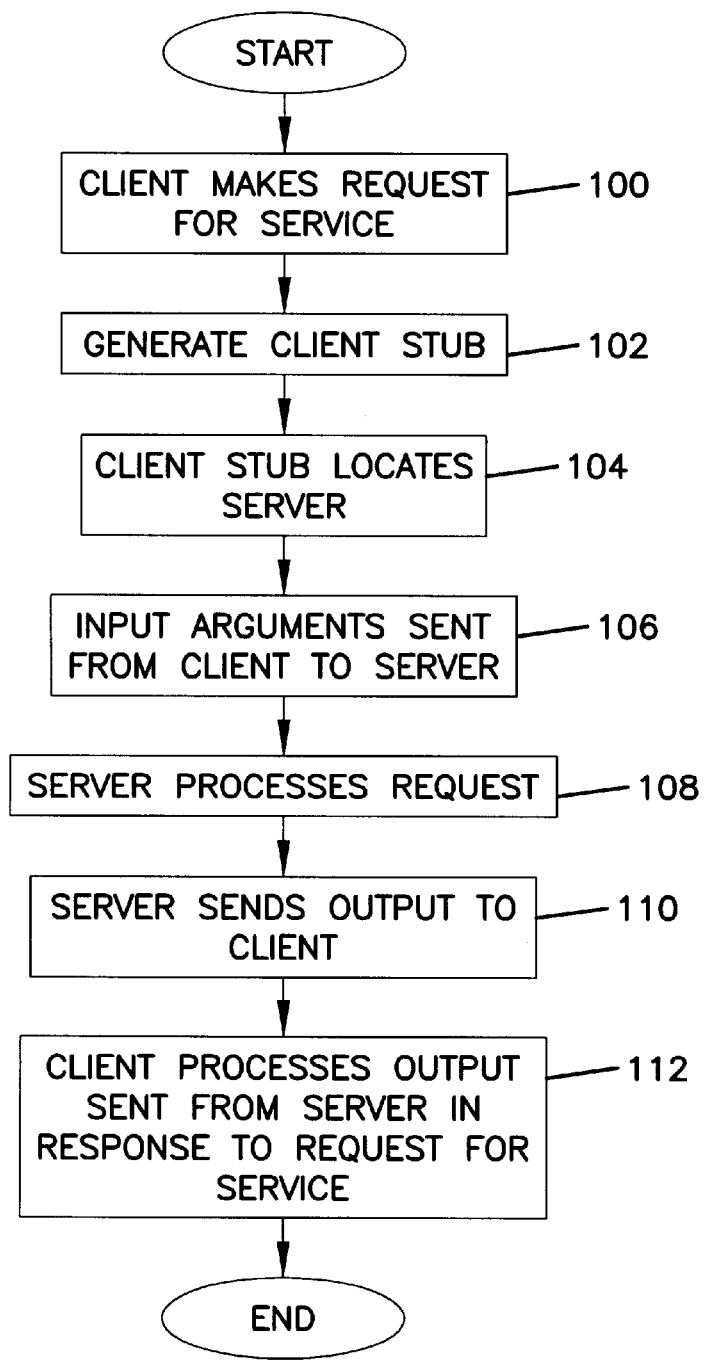
FIG. 4 is a flowchart describing the general method for processing client and server stubs.

Referring to FIGS. 3–6, the request process is initiated when a client makes a request for service (step 100 of FIG. 4). Typically, the request is initiated as an ordinary function call in the operation of the client application. For example, referring to FIG. 3, the client program 54 requests membership information 64. For convenience, the reference numbers of the elements of FIG. 3 will be used to aid in the description, however, it is understood that the example depicted in FIG. 3 is only an example and that many other types of requests are made within a health care transaction network 10. For example, request 64 for member enrollment information may be made by program 54 in the benefit subsystem 30. The benefit subsystem 30 holds information regarding benefit plans. Benefit plans define what services are covered and at what level each service is covered. Following this example and referring to FIG. 3, the benefit subsystem 30 is the client and the enrollment subsystem 26 is the server. Broadly, enrollment subsystem 26 processes benefit subsystem's 30 client request for member enrollment information and returns the information to benefit subsystem 30 appended to server stubs 62.

Referring to FIG. 4 for general functionality, client application makes a service request 64 (step 100). Client stub 60 is generated (step 102). Client stub 60 includes information for the remote procedure call, handling of input arguments and understanding of the client/server context.

Next, the client stub 60 locates the appropriate server to handle the request (step 104). If the client does not know the location of the appropriate server, client stub 60 queries a directory server for the list of locations (hostnames and ports) where a server is available. The directory server listens for client requests and maintain a list of locations of servers registered with the directory server. In response to the client stub 60 query, directory server returns the address (es) of available servers in the network 10. The client stub 60 caches the server address(es) for future requests and for redundancy purposes. If the address of the appropriate server is already cached, client stub 60 uses the cached information to locate the server.

After client stub 60 has located a server (step 104), it sends the client input arguments through the network 10 to its corresponding server stub 62 (step 106). The input arguments typically include a security ticket validating the client. The server then processes the request (step 108). More specifically, server stub 62 unpacks the input arguments and calls the function desired by the client application. For example, in FIG. 3, server program function 66 checks on membership status. Server function 66 returns output arguments (and any error parameters) to the server stub 62 which passes them back to the client stub 60 (step 110). Client stub 60 processes response to the request (step 112). More specifically, the client stub 60 unpacks the output arguments and returns them to the client application (step 112).

It is understood that whether the process is defined as a client process or a server process depends on the context and perspective of the client and server. For example, a server can make requests to other servers, making the process both a server and a client process. Generally, client stubs 60 are responsible for locating a server to handle the request, packaging input arguments and passing them over the network 10 to the server with the validation ticket, waiting for the server to reply and unpacking the return value and output arguments returned by the server. Server stubs 62 are responsible for listening for client requests, unpacking the input arguments, validating server access, calling server function, packaging the return value and output arguments returned by the server code, recording audit information, gathering performance data and passing return value and output arguments back to client stub 60 over network 10.

Figure 5:
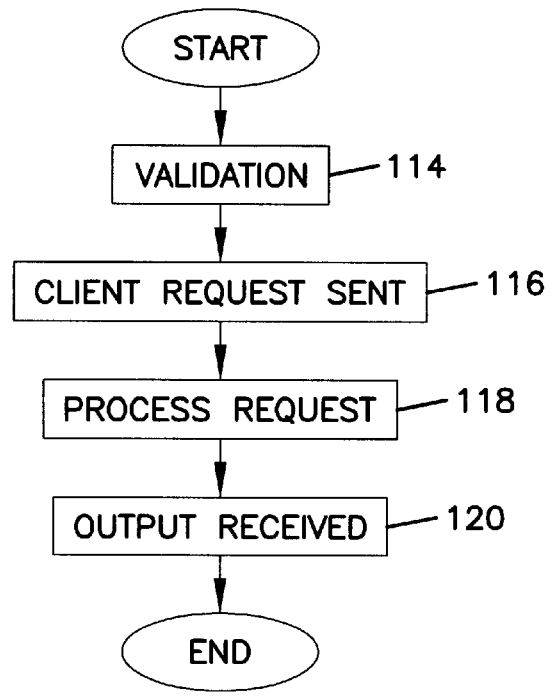
FIG. 5 is a flowchart describing the general method for processing health care transactions in accordance with the present invention.

Referring to FIG. 5, when a client first makes a request, the network 10 first checks that the client is valid (step 114). Once the client is validated, the client requests can be sent through the network 10 (step 116) for processing by a server (step 118) to receive the appropriate output (step 120).

Figure 6:
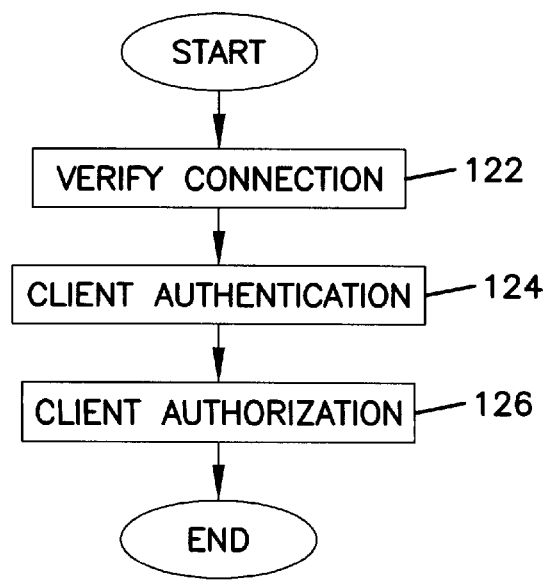
FIG. 6 is a flowchart depicting the Validation step of FIG. 5 in greater detail.

Referring to FIG. 6, the validation step 114 of FIG. 5 is depicted in greater detail. Validation step 114 starts by verifying that the client is connected to the network 10 (step 122). Then, network 10 checks that the client has been authenticated (step 124). More specifically, the network 10 checks whether the client has a valid ticket to request network services. The client stub must present a valid network-generated ticket when making a service request. Those skilled in the art will recognize that the form and contents of a valid ticket may vary depending on the security requirements of network 10.

Once the network 10 authenticates the client, the server checks whether or not the client is authorized to use the interfaces in the server (step 126). More specifically, the server verifies that the specified user is a member of a group that has permissions to perform the requested operation by comparing the ticket contents against the server's own database access control information.

Examples of the specific types of requests made and data flowing through a health care transaction network 10 are shown in FIGS. 7–11. FIGS. 7–10 show the provider contracting subsystem 32 which provides data management functions to build and maintain provider contracting definitions. Definitions managed within the provider contracting subsystem 32 include, for example, information about: health care providers, including physicians, hospitals and dentists; reimbursement agreements between providers and a company; effective dates; contracting entity; contracting companies; fee schedules and rates; rate type, such as, per diem, per hour, per stay, percentage; fee maximums; procedure codes; hospital categories; government health care program information, such as, Medicaid and Medicare; and data relating to costs associated with a medical service but for which a claim has not yet been received.

More specifically, for example, for the fee schedule, the data captured is the rate schedules used by the providers. In particular, the information stored includes a unique id for the fee schedule, a free form description of the schedule, the procedures and maximum fee rates for each procedure code covered in a fee schedule, and a resource based relative value scale rate (pre-determined).

Figure 7:
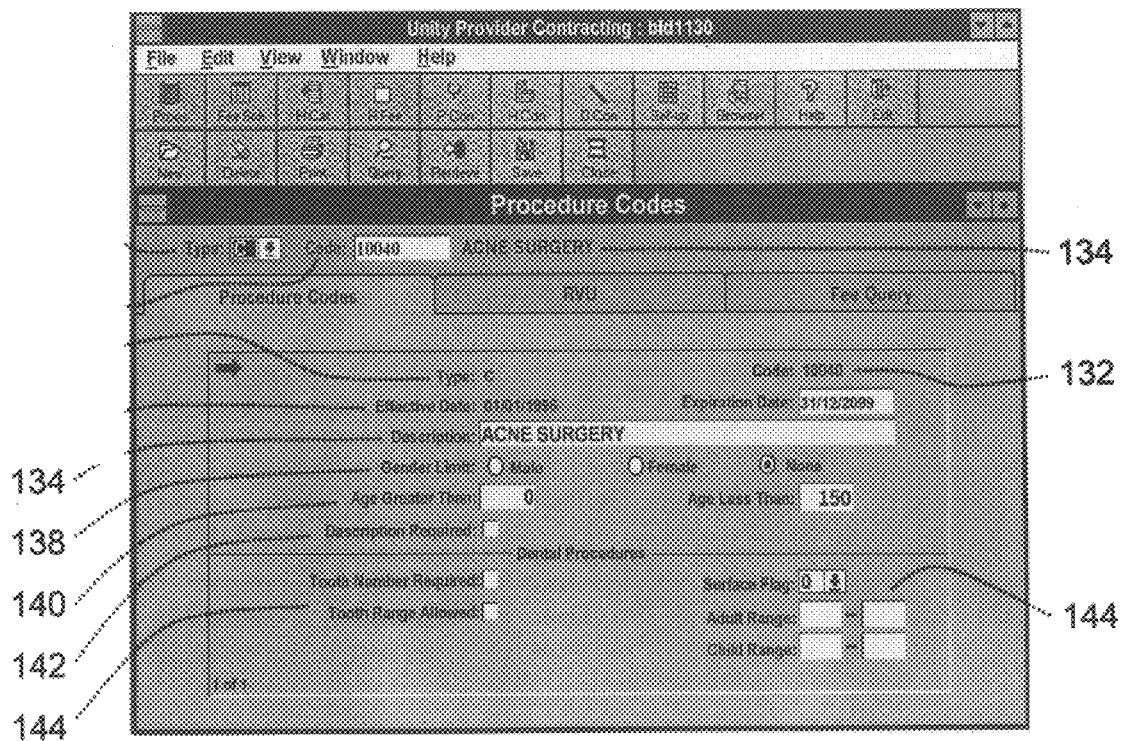
FIG. 7 is a user interface screen depicting user entry of data in the provider contracting subsystem.

The data may be entered in different formats. In the preferred embodiment, the data is entered as shown in FIG. 7. For example, demographic parameters for a particular health care procedure code include the type of procedure 130, specific procedure code 132, text description of procedure code 134, the effective and expiration dates for the use of procedure code 136, any gender limitation for procedure 138, any age limitation for the procedure entered as the limits of an age range 140 and information as to whether additional description is required 142. The specific procedure code is obtained from standard listing of procedure codes updated annually by national medical and insurance associations. Different demographic parameters are required for dental procedures 144.

Figure 8:
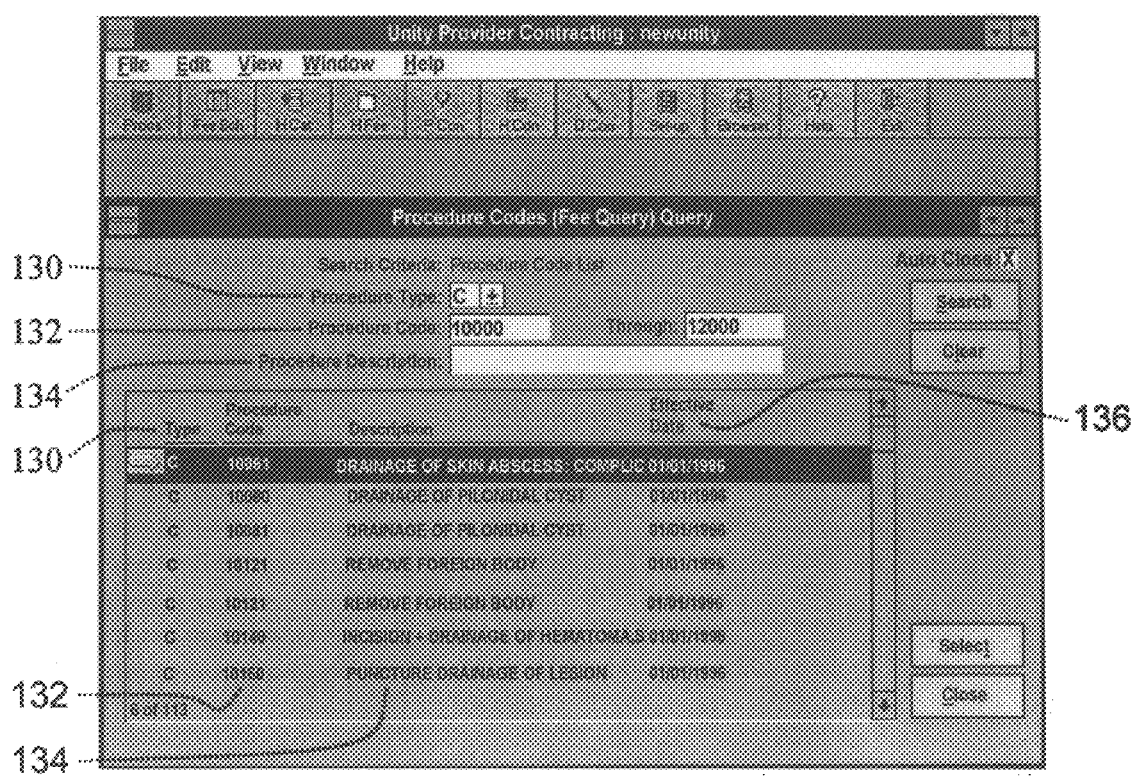
FIG. 8 is a user interface screen depicting entry of a data request in the provider contracting subsystem.
Figure 9:
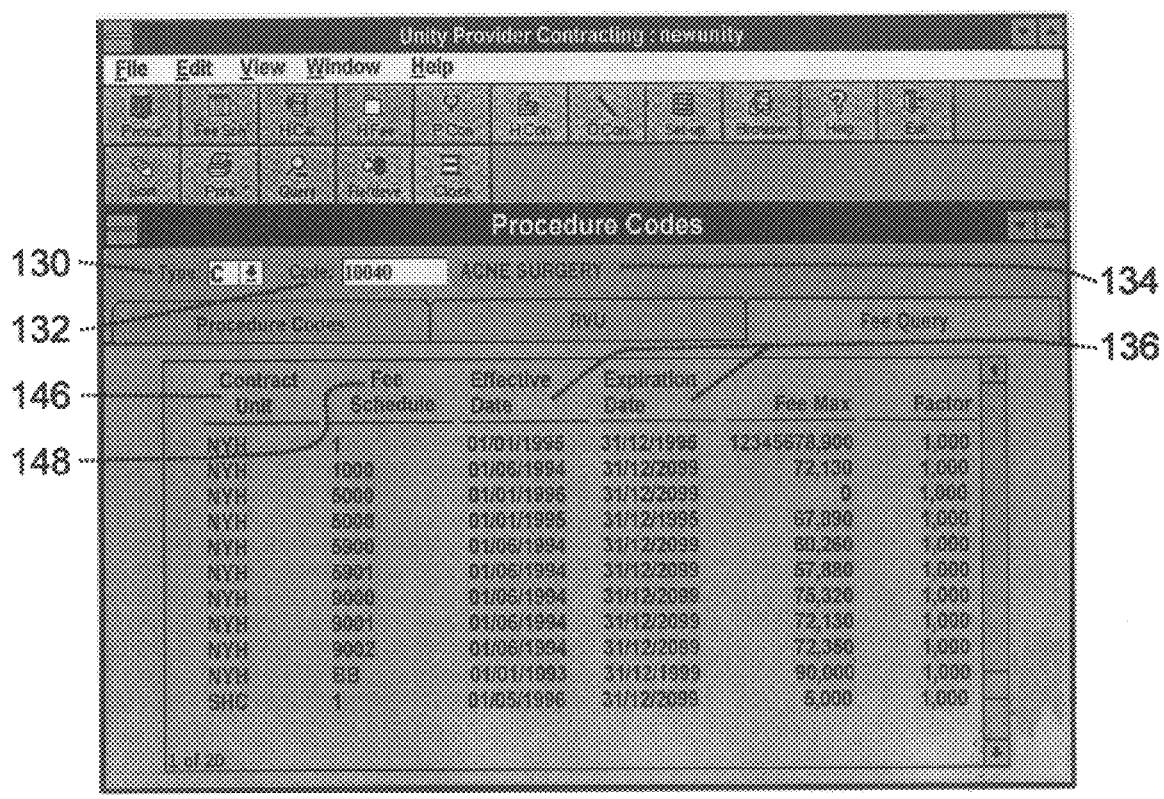
FIG. 9 is a user interface screen depicting the on-line response to the data request of FIG. 8.
Figure 10:
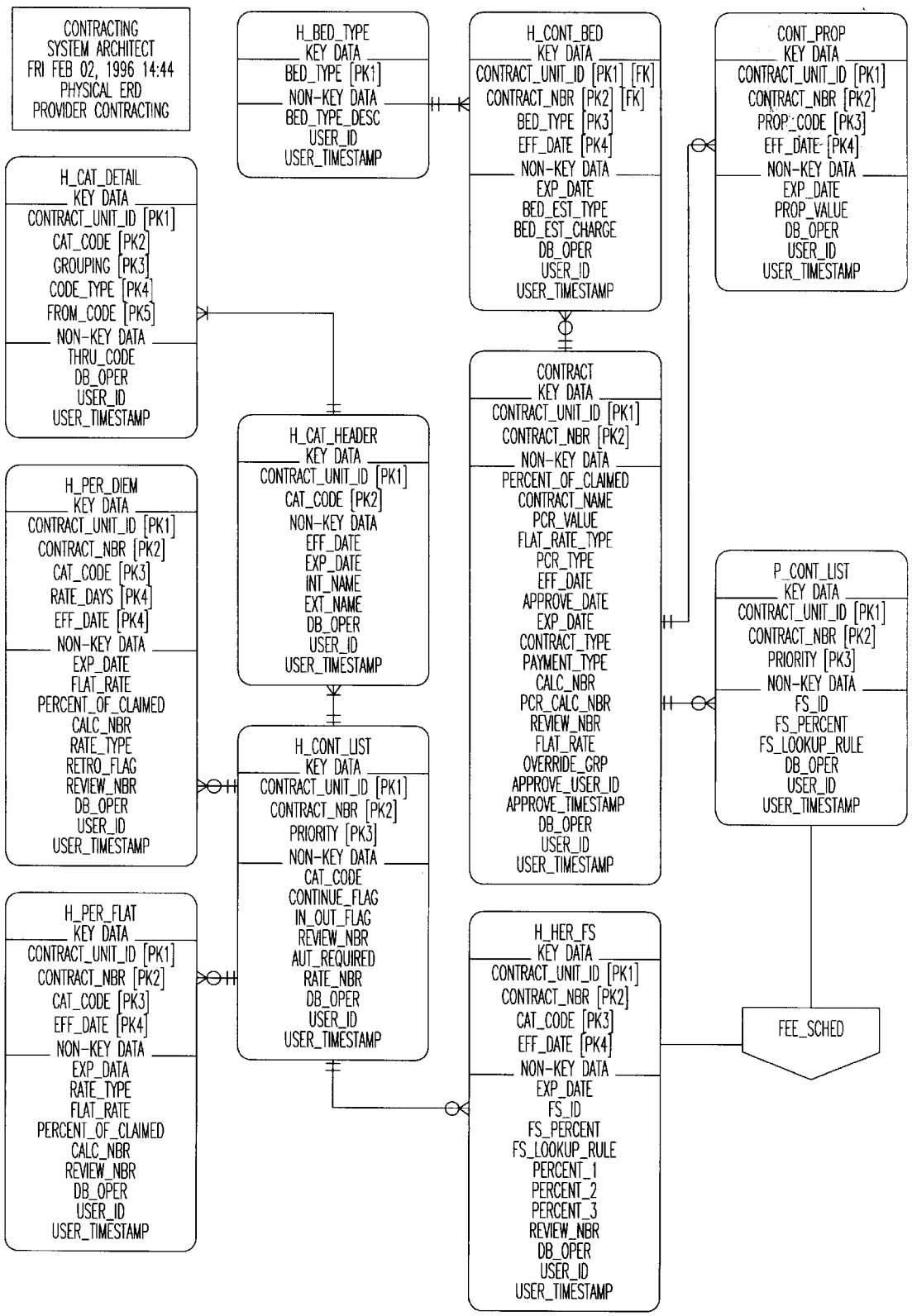
FIG. 10 is a block diagram showing the logical relationships among data within the provider contracting subsystem.

Requests for procedure code fee schedule information are made as shown in FIG. 8. Procedure code information can be obtained by searching for a given procedure type 130, a particular procedure code or range of procedure codes 132 and/or procedure description 134. Procedure code fee information is returned, as shown, for example, in FIG. 9. In FIG. 9 the information is sorted by contract unit 146 and fee schedule 148. Procedure code data is stored in a database system. It is understood that the database system may be a single database system or different database systems. FIG. 10 shows the interconnectiveness of the data, its general storage and access relation to other files. Appendix B provides an example data dictionary listing variable names and descriptions.

Figure 11:
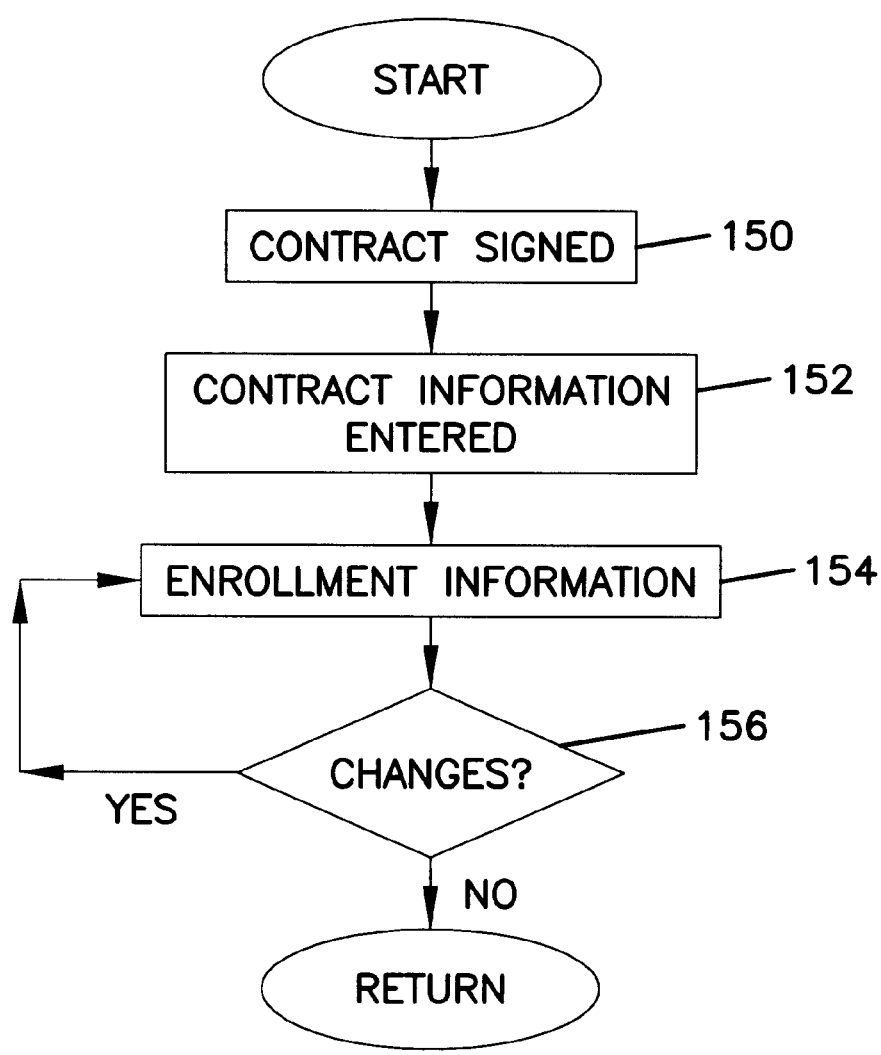
FIG. 11 is a block diagram of the member enrollment subsystem.

In another example, enrollment subsystem 26 establishes and maintains individual membership health care plan enrollment records. Referring to FIG. 11, first a contract for managed care services is signed between an account and a managed care organization (step 150). An account may be an individual, family or company. Next, the contract information is entered into the subsystem 26 (step 152). Next, enrollment form information, provided by each individual member, is entered into the subsystem 26 (step 154). Enrollment additions, changes and terms are each entered as a transaction to the enrollment subsystem 26 (step 156). Enrollment information is retrieved from the enrollment subsystem 26 as needed by other subsystems such as, for example, the benefit subsystem 30.

Although the description of the preferred embodiment has been presented, it is contemplated that various changes could be made without deviating from the spirit of the present invention. Accordingly, it is intended that the scope of the present invention be dictated by the appended claims, rather than by the description of the preferred embodiment.

FROM MERCHANT & GOULD MPLS 612 332 9081    (TUE) 6. 1'99 15:57/ST. 15:56/NO. 4261404772 P 2

Appendix A

```
# $Id: Makefile,v 1.6 1996/12/11 19:26:16 mbell Exp $

# Copyright UNITED HEALTHCARE CORPORATION 1995.
# This software and documentation contain confidential and
# proprietary information owned by United HealthCare Corporation.
# Unauthorized use and distribution are prohibited.

# Sample makefile to be used for servers generated via tpmake.
# vi:set tabstop=8:
# Specify the name of the server. The server binary will be left in a file
# with this name.
PROD_USER=`whoami`

SERVER       = fee_query

# The SQL_PREFIX macro has been left to facilitate use of both 1.0 and
# 1.1 versions of the OEC tools. It's function has been replaced by
# the SQL macro.

SQL_PREFIX   = fsched_query

# The SQL, DB_NAME, DB_TYPE, DB_LOGIN, and DB_PWD macros are used to build
# the $(SERVER).res file required by tpmake.

# SQL - Specifies the name of a file containing SQL statements. The file
#       name must end with a .sql suffix. A C source file will be created
#       for each SQL file. These files will have names that correspond
#       with the SQL file names (e.g., queries.sql results in queries.c
#       being generated).

# DB_NAME - Specifies the name of the database to be accessed by the
#       statements in the corresponding SQL file.

# DB_TYPE - Specifies the type of DBMS where the database resides. This
#       must be one of the following:
#           db2    - DB2/6000
#           sybase - SYBASE

# DB_LOGIN - Specifies the name of a shell environment variable that will
#       contain the login id used to access the database.

# DB_PWD - Specifies the name of a shell environment variable that will
#       contain the password used to access the database.

# NOTE: The 1.1 version of the tools allows a single server to access
# multiple databases. If your server needs to do this, specify multiple
# values for each of thes macros. For example:

# SQL      = syb_queries.sql    db2_queries.sql
# DB_NAME  = claims             calls
# DB_TYPE  = sybase             db2
# DB_LOGIN = SYB_LOGIN          DB2_LOGIN
# DB_PWD   = SYB_PWD            DB2_PWD

# The number of values specified for each of these macros must match.

SQL            = $(SQL_PREFIX).sql
DB_NAME        = `getenv("DB_NAME")`
DB_TYPE        = sybase
DB_LOGIN       = DB_LOGIN
```

```
DB_PWD            = DB_PWD

SQL_TAGS          = $(SQL:.sql=)
SQL_C             = $(SQL:.sql=.c)
SQL_DEF           = $(SQL:.sql=.def)

# Specify the test client name.  If there is no test client
# (e.g., rpcdebug is used for testing the server), specify the keyword
# "none".

CLIENT            = none

# Specify names of all IDL files that should be combined to form the
# IDL definitions for this server.  The makefile will merge the specified
# files into the file $(SERVER).def.  Therefore, you must not have hand
# coded IDL definitions in a file named $(SERVER).def.

# Some commonly used definitions for IDL_SRCS are:

# IDL_SRCS = $(SQL_DEF)

#       All IDL definitions are generated from SQL via sqlmake.

# IDL_SRCS = my.def

#       All the IDL definitions for the server have been hand coded.  No
#       IDL definnitions will be generated from the SQL definitions.

# IDL_SRCS = my.def $(SQL_DEF)

#       The hand coded IDL will be merged with IDL generated by sqlmake
#       to create the server's IDL definitions.

IDL_SRCS          = fs_query.def

# Specify the version identifier to place in the generated IDL file.

# NOTE: This may not be left blank

IDL_VERSION       = 1.0

# The DATABASE macro has been left to facilitate use of both 1.0 and
# 1.1 versions of the OBC tools.  It's function has been replaced by
# the DB_NAME macro.

DATABASE          = newunity

# Specify the name of the application as it appears in the authentication
# maps.  This value is used by the code generated to validate application
# tickets.  If this server does not require application tickets, leave the
# application name blank.

APPL_NAME         = unty

# Specify the type of ticket required.  This must be either global_ticket
# or appl_ticket.

TKT_TYPE          = appl_ticket
```

```
# Specify the name of a global string variable that will hold the ticket
# that may be required to access functions in the server. If none of the
# server functions require ticket validation, this can be left blank.

# NOTE: PowerBuilder applications will have to manually declare this global
#       variable.

TKT_NAME         = g_sSec_appltkt

# List all server functions that do not require ticket authentication.
# The default is to require a valid ticket for access. Specify the
# keyword "all" to prevent the addition of ticket handling code.

# NOTE: If you will be testing the server via rpcdebug, you must specify
#       NO_TICKET=all when building the test server. This can be done on
#       the make command line, there is no need to change the makefile
#       to build a test server (e.g., make NO_TICKET=all).

NO_TICKET        =

# If you want to turn error logging on for this server, specify the
# keyword "yes". Otherwise leave it blank, the default here.

ERROR_LOGGING    = yes

ESCAPEQUOTES     = on

# To use message catalogs, place the prefix name of the message source
# file here. The prefix name is the same as the Unity subsystem prefixes.
# i.e. ben, enr ... The message source file and the message Makefile
# should already be placed in a subdirectory of the same prefix name
# in the path ($WORK_ROOT)/unity/msg .

#       (e.g. for the subsystem prefix name "xyz" )

#       "$(WORK_ROOT)/unity/msg/xyz/xyz.msg" where the
#       message source file name is   xyz.msg   and
#       MESSAGES = xyz .

#       Add the following definition file format in
#       the server's include list:
#       #include "xyz_msg.h"

#       Refer to ($WORK_ROOT)/unity/msg/README for more information.

#       Be sure the WORK_ROOT environment setting is set to "$HOME/work".

MESSAGES         = prv

MESSAGES_H       = $(MESSAGES:=_msg.h)

# List any functions that require auditing. If the keyword "all" is
# specified, every function call will be audited. By default, functions
# will not be audited.

AUDIT            =

# Specify the name of a function to be called during server initialization.
# If you do not need a function called during server initialization, leave
```

```
# this blank.

# NOTE: Servers generated by tpmake include a function named $(SERVER)_init
#       that must be called to initialize the server. If you change the
#       SRVR_MAIN definition to call your own initialization function,
#       your function must call $(SERVER)_init.

# NOTE: This macro is not used by the 1.0 build process.

SRVR_MAIN       = init_nls_func

# Specify the name of a function to be called during server shutdown.
# If you do not need a function called during server shutdown, leave
# this blank.

# NOTE: Servers generated by tpmake include a function named $(SERVER)_end
#       that must be called to cleanup the server. If you change the
#       SRVR_CLEANUP definition to call your own cleanup function, your
#       function must call $(SERVER)_end.

# NOTE: This macro is not used by the 1.0 build process.

SRVR_CLEANUP    = $(SERVER)_end

# Specify types of server and client stubs to be generated.
# currently build C server stubs, C client stubs, PowerBuilder client stubs,
# and Perl client stubs.

SRVR_STUB       = $(SERVER)_s.c
CLNT_STUBS      = $(SERVER)_c.c \
                  $(SERVER)_c.pl

# Specify the source files that make up the server.

# NOTE: Do not remove the reference to transac.c; it is required for
#       code generated by tpmake.

SRVR_SRCS       = \
                  fs_query.c \
                  $(SRVR_STUB) \
                  $(SQL_C) \
                  transac.c \
                  fs_query_nls.c

Specify the components that make up the client (if there is one).

CLNT_SRCS       = $(CLIENT).c \
                  $(SERVER)_c.c

Specify any man pages to be installed with this server.

MANPAGES        = $(SERVER).1

# Specify the top of the installation directory. The install target is
# set up to install files relative to this directory. The default is
# correct for most servers.

WHEREIGO        = $(DESTROOT)/usr/dce
MANDIR          = $(DESTROOT)/usr/man/man1
```

```
# Define the list of object files needed for the server and client.
# The default is correct for all servers.

SRVR_OBJS      = $(SRVR_SRCS:.c=.o)
CLNT_OBJS      = $(CLNT_SRCS:.c=.o)

# Define options used on cc commands.  The default is correct for most
# servers.

# NOTE: To compile the program with debug tables, specify "MAXOPT=-g" on the
#       make command.  The ECFLAGS macro allows you to specify other options
#       and to override default options when necessary.

MAXOPT         = -s
DEFINES        = $(DCE_DEFINES)
INCLUDE        = $(DCE_INCLUDES) -I$(IIS_DCE_TOOLS)/include
LIBDIRS        = $(DCE_LIB_DIRS) -L$(IIS_DCE_TOOLS)/lib  $(LOCAL_LIB_OPTION)
CFLAGS         = $(MAXOPT) $(DEFINES) $(INCLUDE) $(LIBDIRS) $(ECFLAGS)

# List of libraries to be searched when loading the server or client.

# NOTE: You must not remove either of the default values.

LIBS           = $(SYBASE_LIB) $(DCE_LIBS) $(UNTY_LIBS) $(LOCAL_LIB_NAME)

Rules for required targets.

all: $(MESSAGES_H) stubs client server install: all
        $(INSTALL_SERVER) $(SERVER) $(IDL_VERSION) $(WHEREIGO)
        touch $(SERVER).1
        $(INSTALL_MAN_PAGES) $(MANDIR) $(MANPAGES)

clean:
        rm -rf  $(SQL_C) $(SQL_PREFIX).h $(SERVER)_funcs.h transac.c
        rm -rf  $(SRVR_OBJS) $(CLNT_OBJS)
        rm -rf  $(SRVR_STUB) dbms.h warning
        rm -rf  $(SERVER).res $(SERVER).def $(SQL_PREFIX).def
        rm -rf  *.time clobber: clean
        rm -rf  $(SERVER) $(CLIENT) $(CLNT_STUBS) $(SERVER).h server: $(SERVER)

these:
        echo $(MESSAGES_H)

client: $(CLIENT)_check stubs: $(SRVR_STUB) $(CLNT_STUBS)

LOCAL_LIB_OPTION       =       -L$(LOCAL_LIB_DIR)
LOCAL_LIB_NAME  =      -lprvlib
LOCAL_LIB              =       libprvlib.a
LOCAL_LIB_DIR   =      $(WORK_ROOT)/unity/prv/lib

# Pick up the common macro definitions and make rules
```

```
# Define the list of object files needed for the server and client.
# The default is correct for all servers.

SRVR_OBJS       = $(SRVR_SRCS:.c=.o)
CLNT_OBJS       = $(CLNT_SRCS:.c=.o)

# Define options used on cc commands.  The default is correct for most
# servers.

# NOTE: To compile the program with debug tables, specify "MAXOPT=-g" on the
#       make command.  The ECFLAGS macro allows you to specify other options
#       and to override default options when necessary.

MAXOPT          = -g
DEFINES         = $(DCE_DEFINES)
INCLUDE         = $(DCE_INCLUDES) -I$(IIS_DCE_TOOLS)/include
LIBDIRS         = $(DCE_LIB_DIRS) -L$(IIS_DCE_TOOLS)/lib $(LOCAL_LIB_OPTION)
CFLAGS          = $(MAXOPT) $(DEFINES) $(INCLUDE) $(LIBDIRS) $(ECFLAGS)

# List of libraries to be searched when loading the server or client.

# NOTE: You must not remove either of the default values.

LIBS            = $(SYBASE_LIB) $(DCE_LIBS) $(UNTY_LIBS) $(LOCAL_LIB_NAME)

Rules for required targets.

all: $(MESSAGES_H) stubs client server install: all
        $(INSTALL_SERVER) $(SERVER) $(IDL_VERSION) $(WHEREIGO)
        touch $(SERVER).1
        $(INSTALL_MAN_PAGES) $(MANDIR) $(MANPAGES)

clean:
        rm -rf $(SQL_C) $(SQL_PREFIX).h $(SERVER)_funcs.h transac.c
        rm -rf $(SRVR_OBJS) $(CLNT_OBJS)
        rm -rf $(SRVR_STUB) dbms.h warning
        rm -rf $(SERVER).res $(SERVER).def $(SQL_PREFIX).def
        rm -rf *.time clobber: clean
        rm -rf $(SERVER) $(CLIENT) $(CLNT_STUBS) $(SERVER).h server: $(SERVER)

these:
        echo $(MESSAGES_H)

client: $(CLIENT)_check stubs: $(SRVR_STUB) $(CLNT_STUBS)

LOCAL_LIB_OPTION    =       -L$(LOCAL_LIB_DIR)
LOCAL_LIB_NAME      =       -lprvlib
LOCAL_LIB           =       libprvlib.a
LOCAL_LIB_DIR       =       $(WORK_ROOT)/unity/prv/lib

# Pick up the common macro definitions and make rules
```

```
include $(UHC_DCE_TOOLS)/include/dcel_common_...
include $(UHC_DCE_TOOLS)/include/dcel_current_stubs
include $(UHC_DCE_TOOLS)/include/dcel_make_rules
include $(UHC_DCE_TOOLS)/include/dcel_sql_make_rules

Place any server specific dependency rules and/or targets after this comment.

The following includes are unity specific.

include $(WORK_ROOT)/unity/include/unty_make_rules
include $(WORK_ROOT)/unity/include/unty_common_defs

# These includes are for makeing "generic" servers.
# Uncomment and customize as required.

# SUBSYS              - your_subsystem_name
# SQL_LOG_FILE        = text_file_name_which_includes_those_tables_to_be_logged
SUBSYS_LOG_DTM      = the_name_of_the_resulting_dtm_file_for_the_logged_tables include $(WORK_ROOT)/unity/include/unty_ctm_rules
```

APPENDIX B

Data Dictionary

Appendix to Figure 10

| Table Name | Description |
|---|---|
| cont_prop | Properties for contracts - i.e. admin, hold. |
| cont_unit | Contract Unit Setup Table. This tables defines the valid contract units. |
| contract | Contracts header information for physician, hospital and dental contracts. |
| fee_sched | Fee schedule header information for physician, hospital and regional fee schedules. |
| fees | Physician fee schedules' rates (fee max) by procedure codes. |
| fs_by_postal | Criteria to define the fee schedule associated to regions (by postal code). |
| fs_rbrvs | Resource Based Relative Value Master. Contains RBRVS values associated to procedure codes and fee schedules. |
| fs_rvu | Relative Value Master. Contains RVU values associated to procedure codes. |
| h_bed_type | Global table listing bed types and descriptions. |
| h_cat_detail | Hospital Category Detail. Contains the detail which defines a hospital service code category for a contract unit. Used to determine claims payment rates (Hospital contracting). |
| h_cat_header | Hospital Category Header. Contains the hospital service code categories setup for a contract unit, used to determine claims payment rates. |
| h_cont_bed | Continuation of the Hospital Contract - lists the bed types and estimates for the bed type for IBNR reporting purposes. |
| h_cont_list | Continuation of the Hospital contract. Contains the "list" of service categories and the order to use them (priority). Service Categories for hospital contracts are used to determine claims payment rates and rules. |
| h_per_diem | Continuation of the Hospital contract. Contains the per day/per stay/per hour schedule information for hospital contracts (used when h_cont_list.rate_nbr = 1). |
| h_per_flat | Continuation of the Hospital contract. Contains the fee schedule information for hospital contracts (used when h_cont_list.rate_nbr = 3). |
| h_per_fs | Continuation of the Hospital contract. Contains the fee schedule information for hospital contracts (used when h_cont_list.rate_nbr = 2). |
| hfs_fees | Hospital Fee Schedule Fees. Contains the fee max for a grouping of procedure codes. Used in conjunction with h_per_fs and hfs_grouping. |
| hfs_grouping | Hospital Fee Schedule Groupings. Contains the range of procedure codes assigned to groupings. Used in conjunction with h_per_fs and hfs_fees tables. |
| p_cont_list | Continuation of Physician and Dental contracts. Contains the "list" of fee schedules to use and the order to use them (priority). |
| proc_code | Procedure Code Master File. Contains procedure code description and limitations (gender and age). |
| proc_type | Global table listing procedure code types and descriptions. |
| prv_control | Global table listing the "controls" used for processing rules. Currently the only control is which property code denotes Administrative Hold for a contract. |
| prv_prop_list | Global table listing the valid property codes and descriptions for provider contracting. |

| Column Name | Attributes | Description |
|---|---|---|
| continue_flag | smallint | Indicates whether or not to continue looking for other categories to match. '0' indicates once the system makes a match, it should not continue to look for another category. '1' indicates the system should continue to check to see if the claim matches any of the other categories. This allows the system to make more than one rate payment on the same claim. Valid values are:<br>0 - N - no<br>1 - Y - yes<br>default is 0 |
| contract_name | char (40) | A descriptive name of the contract. |
| contract_nbr | int | The unique identifier for a contract. A contract consists of several parameters required for claims payment. The values of the parameters when combined make the contract unique. |
| contract_type | smallint | Indicates the type of contract, valid values are:<br>0 - D - Dental<br>1 - H - Hospital<br>2 - P - Physician (non-hospital and non-dental) |
| contract_unit_id | char (3) | A unique id for a contract unit. A contract unit is the entity that defines/contracts fee arrangements with a provider network. A contract unit can be a business unit or it can be another entity such as HCFA, an individual state, a national entity, etc. |
| contract_unit_name | char (40) | The name of the contract unit. |
| country_code | char (3) | A short code to uniquely identify each country. |
| db_oper | char (1) | Code for the type of database operation, used internally for audit purposes. |
| desc_reqd_flag | smallint | Indicates if a more descriptive procedure description is required at claims entry if the procedure code is a generic procedure code. Validated against the code_list.list_id = "yesno" as follows:<br>0 - N - no - no description is required<br>1 - Y - yes - yes a more descriptive description is required at claims entry<br>default is 0 |
| eff_date | datetime | The first day the timeline for an entity is active. A timeline represents data for a specific date range. |
| exp_date | datetime | The last day the timeline for an entity is active. A timeline represents data for a specific date range. |
| ext_name | char (40) | Description of categories/services external to the Business Unit/Contract Unit. |
| factor | float | A multiplier used in the contracting subsystem to calculate the fee max when using RBRVS. |
| fee_max | float | The maximum amount a provider may be paid for a specific health care service provided to covered person under a specific contract. |
| flat_rate | float | The rate amount for flat rate contracts. Note all procedures will be charged this one amount (if used). |
| flat_rate_type | smallint | Indicates if the flat rate is a per day rate or a rate by procedure. Valid values are:<br>1 - P - Procedure<br>default is 1 |
| from_code | char (20) | The lowest value of the data element for a range in the criteria definition. |

| Column Name | Attributes | Description |
|---|---|---|
| age_gtr_limit | smallint | Used for age limitation, age greater than the value entered indicates not covered procedure code. |
| age_less_limit | smallint | Used for age limitation, age less than value entered indicates not covered procedure code. |
| approve_date | datetime allow null | The date the contract was approved by a supervisor and ready to be used for claims processing. |
| approve_timestamp | datetime allow null | Date and time the approval was entered. |
| approve_user_id | char (15) | user_id of the supervisor who approved the contract. |
| aut_required | smallint | Indicates if an authorization is required for the category. Valid values are:<br>0 - N - no<br>1 - Y - yes<br>default is 0 |
| bed_est_charge | float | The estimated charge per day for the bed type. Used for IBNR reporting. |
| bed_est_type | smallint | The type of estimate charge, valid values are:<br>0 - D - per diem<br>1 - H - per hour<br>2 - S - per stay<br>default is 0 |
| bed_type | char (10) | Unique identifier for a hospital bed type. |
| bed_type_desc | char (40) | Description for the hospital bed type. |
| calc_nbr | smallint | Unique identifier to indicate the formula to use when calculating the claim payable amount. Values are validated against code_list table. |
| cat_code | smallint | A unique key to represent a category of services. Hospital services are grouped into a category within the Unity Provider Contracting subsystem. Examples of hospital categories are: burn unit, mental health/chemical dependency, maternity, etc. |
| code_type | char (5) | Indicates the type of code range used for a hospital category criteria. Example, R indicates the from_code and thru_code range is a revenue code range, A= indicates the from_code and thru_code range is an age range where the criteria matches if the patient's age is within the age range, etc.. Abbreviations are stored in database. Valid codes are:<br>0 - HOS - Hospital Codes<br>1 - PS - Patient Status<br>2 - PA - Pre-authorization Admit Types<br>4 - C - Procedure Codes<br>10 - ID - Diagnosis Code<br>11 - D1 - Primary Diagnosis Code<br>12 - D2 - Primary or Secondary Diagnosis Code<br>13 - A= - Patient Age equal to<br>14 - A> - Patient Age greater than<br>15 - A< - Patient Age less than<br>16 - AC - Claimed Amount exceeds<br>18 - ZZ - Default (A default category is always setup on a hospital contract as the last priority to establish a default rate for the contract). |

| Column Name | Attributes | Description |
|---|---|---|
| percent_of_claimed | float | The percent of claimed amount. Used to calculated contract amount (amount_claimed * percent_of_claimed / 100 = contract amount) or lesser of percent of amount claimed or fee max. |
| percent_1 | float | The percentage amount to pay for the highest dollar procedure (or grouping). |
| percent_2 | float | The percentage amount to pay for the second highest dollar procedure (or grouping). |
| percent_3 | float | The percentage amount for the third highest dollar procedure (or grouping). |
| postal_from | char (10) | The lowest value of a postal code range. |
| postal_thru | char (10) | The highest value of a postal code range. |
| priority | smallint | The priority given to an entity in a table. The priority establishes the search sequence. |
| proc_code | char (10) | An identifier for medical service (procedure). Procedure codes can be CPT codes (Physician's Current Procedural Terminology codes), CDT codes (Current Dental Terminology codes), procedure codes unique to a country, etc. The combination of procedure code type and procedure code identifies a unique procedure. |
| proc_code_desc | char (60) | Free form text description for the procedure code. |
| proc_code_from | char (10) | The lowest value of a procedure code range. |
| proc_code_thru | char (10) | The highest value of a procedure code range. |
| proc_code_type | char (1) | The type of procedure code. A procedure code type can be a CPT (Physician's Current Procedural Terminology) type, CDT (Current Dental Terminology) type, ICD-9 (International Classification of Diseases, 9th edition) procedure type, etc. The combination of procedure code type (proc_code_type) and procedure code (proc_code) identifies a unique procedure. |
| proc_type_desc | char (30) | Free form text description for the procedure code type. |
| prop_code | smallint | A unique code assigned to a property. Properties establish information that pertains to an entity, but does not apply to all entities. (i.e., administrative hold, alternate Ids, etc.). |
| prop_value | char (30) | The value of the property. This value could contain why an entity is on administrative hold, the entity's alternate Id, etc. |
| rate_days | smallint | Indicates the day the rate of payment begins. |
| rate_nbr | smallint | Indicates whether the rates are based on per diem/per stay/per hour or based on a fee schedule. Valid values are:<br>1 - D - Per Diem (rates based on per diem/per stay/per hour schedule)<br>2 - FS - Per Fee Schedule (rates based on a fee schedule)<br>3 - FA - Flat Amount (rates based on a flat rate) |
| rate_type | smallint | Indicates the type of rate for the category. Valid values are:<br>0 - D - per diem (valid for rate_nbr 1)<br>1 - H - per hour (valid for rate_nbr 1)<br>2 - S - per stay (valid for rate_nbr 1)<br>3 - P - percentage (valid for rate_nbr 1 and 3)<br>4 - A - flat amount (valid for rate_nbr 3) |
| rbrvs_flag | smallint | Indicates if the fee max value was derived/calculated using RBRVS (Resource Based Relative Value Scale). Values are validated against code_list.list_id = "manualsystem". |

| Column Name | Attributes | Description |
|---|---|---|
| fs_desc | char (40) | A descriptive name for the fee schedule (i.e. Medicare, Medicaid Region A, Medicaid Region B, etc.). |
| fs_id | char (5) | A unique id for a fee schedule. A fee schedule is a listing of codes and related services with pre-established payment amounts. |
| fs_lookup_rule | smallint | Used to identify how to retrieve (or lookup) fee schedule information.<br>1 - P - Physician Fee Schedule<br>2 - R - Regional Fee Schedule (also known as National Fee Schedule)<br>3 - H - Hospital Fee Schedule |
| fs_percent | float | Used to adjust a fee max amount for overhead costs and geographical differences. |
| fs_percentile | smallint | The percentile for the region (i.e. 95th percentile of the Boston region). |
| gender_limit | smallint | Used for gender limitation, values are validated against the code_list.list_id = "genderlimit" as follows:<br>0 - M - male - indicates the procedure covered for males only<br>1 - F - female - indicates the procedure covered for females only<br>2 - N - indicates the procedure covered for both male and females - no limitation<br>default is 2 |
| grouping | smallint | This number is used to group together rows of criteria (hospital category criteria). When setting up criteria, rows with the same grouping value use "or" logic and rows with different grouping values use "and" logic. For example, Revenue code 100 or Revenue code 110 and CPT code 10040 would be set up as follows:<br>1  R  100    100<br>1  R  110    110<br>2  C  10040  10040. |
| in_out_flag | smallint | Identifies whether the category applies to Inpatient claims (I), Outpatient claims (O), or both (B) types of claims for the category. Valid values are:<br>0 - I - Inpatient<br>1 - O - Outpatient<br>2 - B - Both<br>default is 0 |
| int_name | char (40) | Description of services/categories internal to the Business Unit/Contract Unit. |
| payment_type | smallint | Defines how the payment is to be made, valid values are:<br>0 - F - fee-for-service<br>1 - C - capitated primary care providers<br>2 - P - capitated specialists<br>Note: only 0 will be valid for phase I. |
| pcr_calc_nbr | smallint | Unique identifier to indicate the formula to use when calculating the pcr amount. Values are validated against code_list table. |
| pcr_type | smallint | Indicates if the Physician Contingency Reserve (pcr, also known as withhold, refer to The Managed Care Resource - A Glossary of Terms for the definition of PCR) is a percent or flat rate. Valid values are:<br>0 - F - flat rate<br>1 - P - percent<br>default is 0 |
| pcr_value | float | Physician Contingency Reserve (PCR) rate. pcr_type indicates if value is a percent or a flat rate. |
| per_day_limit | smallint | Used for limiting the number of units of a procedure covered per day. |

| Column Name | Attributes | Description |
| --- | --- | --- |
| retro_flag | smallint | Indicates if the rate should be applied to previous days also, or just applied to current and future days. Valid values are:<br>0 - N - apply to current and future days.<br>1 - Y - apply to previous days, current day, future days.<br>default is 0 |
| review_date | datetime | The date the fee amount was last reviewed and/or changed. |
| review_nbr | smallint | The review number to apply to claims. This feature is optional and should be used with discretion. It implies manual intervention for processing of claims. |
| rvu | float | Relative Value Unit. Introduced by HCFA to reimburse physicians' fees based on the amount of time and resources expended in treating patients (without adjustments for overhead costs and geographical differences). RVUs are setup at the procedure code level (not the fee schedule level). |
| surface_flag | smallint | Indicates the number of surfaces the procedure can apply to. Used for dental procedure codes (proc_code_type = "D"). Valid values are:<br>0 - invalid/not required<br>1<br>2<br>3<br>4<br>5 |
| thru_code | char (20) | The highest value of the data element of a range for the criteria definition. |
| tooth_adult_from | char (2) | The lowest value of an adult tooth number range. Used for dental procedure codes (proc_code_type = "D") to determine if the procedure can apply to a specific tooth. |
| tooth_adult_thru | char (2) | The highest value of an adult tooth number range. Used for dental procedure codes (proc_code_type = "D") to determine if the procedure can apply to a specific tooth. |
| tooth_child_from | char (1) | The lowest value of a child tooth number range. Used for dental procedure codes (proc_code_type = "D") to determine if the procedure can apply to a specific tooth. |
| tooth_child_thru | char (1) | The highest value of a child tooth number range. Used for dental procedure codes (proc_code_type = "D") to determine if the procedure can apply to a specific tooth. |
| tooth_nbr_flag | smallint | Indicates if a tooth number is required when submitting a claim with the procedure code. Used for dental procedure codes (proc_code_type = "D"). Valid values are:<br>0 - N - No<br>1 - Y - Yes |
| tooth_range_flag | smallint | Indicates if a tooth range is allowed when submitting a claim with the procedure code. Used for dental procedure codes (proc_code_type = "D"). Valid values are:<br>0 - N - No<br>1 - Y - Yes |
| user_id | char (15) | A unique Id for each person or process that inserted or modified data in the database table. |
| user_timestamp | datetime | The date and time an update or insert occurred in the database table. |

We claim:

1. A system including a computer system and a user program for processing health care transactions in response to a user request in a heterogeneous, distributed computing network, comprising:

a plurality of subsystems each corresponding to an aspect of health care transactions and each facilitating at least one transaction;

a communication interface for exchanging health care transaction information among said plurality of subsystems, said communication interface including communication logic modules comprised of:

(a) a user interface logic module for collecting user inputs and presenting transaction outputs;

(b) a data access logic module for data storage and retrieval, said data access tier including one or more databases of health care transaction information;

(c) a transaction logic logic module for applying a predetermined set of transaction procedures to said user inputs and said database of health care transaction information resulting in transaction output;

an electronic network connecting said user interface logic module to said data access logic module and to said transaction logic module, said data access logic module to said user interface logic module and to said transaction logic module and said transaction logic module to said user interface logic module and to said data access module; and said communication interface including an interface definition language generating transaction-specific communication codes whereby data is exchanged between said subsystems through a common interface structure regardless of the origin of the data.

2. The system of claim 1 wherein the user program of said user interface tier operates in a graphical user interface environment.

3. The system of claim 1 wherein said databases of said data access tier are relational databases.

4. The system of claim 1 further including one or more functional subsystems connected to the electronic network, each subsystem including said user interface tier, said data access tier, said transaction logic tier and said communication interface.

5. A method for processing health care transactions in response to a user request in a heterogeneous, distributed computing network, said network including a plurality of subsystems each corresponding to an aspect of the health care transactions and each facilitating at least one transaction, a communication interface for exchanging health care transaction information, a user interface tier having a computer system and user program, a data access tier including one or more databases of health care transaction information, a transaction logic tier said method for processing health care transactions including a predetermined set of transaction procedures, comprising the computer-implemented steps of:

(a) initiating a transaction in response to user request;

(b) generating transaction-specific communication codes according to a predetermined common interface structure;

(c) appending the communication codes to the transaction information; and (d) transferring health care transaction information among said user interface tier, said data access tier and said transaction logic tier to generate transaction output.

6. The method of claim 5 step (d) further including the computer-implemented steps of:

(d1) processing said health care transaction information in said transaction logic tier to generate transaction output;

(d2) generating transaction-specific server communication code in response to transaction output created;

(d3) appending server communication code to transaction output.

7. The method of claim 5 further including the computer-implemented step of:

(e) providing transaction output to user.

8. The method of claim 7 wherein step (e) is implemented by displaying the transaction output to said user via a computer monitor.

9. The method of claim 7 wherein step (e) is implemented by presenting the transaction output to said user via a printer.

10. The method of claim 7 wherein step (e) is implemented by presenting the transaction output to said user via electronic mail.

11. The method of claim 7 wherein step (e) is implemented by presenting the transaction output to said user via facsimile machine.

* * * * *